United States Patent
Leach et al.

(10) Patent No.: US 6,586,011 B2
(45) Date of Patent: Jul. 1, 2003

(54) MICROENCAPSULATED PLASMINOGEN ACTIVATORS

(75) Inventors: Jonathan K. Leach, Norman, OK (US); Edgar O'Rear, Norman, OK (US)

(73) Assignee: Southpac Trust International, Inc., Rarotonga (CK)

( * ) Notice: Subject to any disclaimer, the term of this patent is extended or adjusted under 35 U.S.C. 154(b) by 0 days.

(21) Appl. No.: 10/176,294

(22) Filed: Jun. 18, 2002

(65) Prior Publication Data

US 2002/0155160 A1 Oct. 24, 2002

Related U.S. Application Data

(63) Continuation of application No. 09/592,482, filed on Jun. 9, 2000, now abandoned.
(60) Provisional application No. 60/139,322, filed on Jun. 10, 1999.

(51) Int. Cl.$^7$ .............................. A61K 9/16; A61K 9/50
(52) U.S. Cl. .................. 424/489; 424/490; 424/493; 424/497; 424/484; 424/486; 424/488; 424/422; 424/423; 424/426
(58) Field of Search ........................... 424/489, 423, 424/490, 426, 491, 488, 493, 451, 497, 499, 501, 422, 484, 486

(56) References Cited

U.S. PATENT DOCUMENTS

| | | | |
|---|---|---|---|
| 5,078,994 A | | 1/1992 | Nair et al. |
| 5,470,582 A | | 11/1995 | Supersaxo et al. |
| 5,503,850 A | * | 4/1996 | O'Rear, III et al. ........ 424/450 |
| 5,879,713 A | | 3/1999 | Roth et al. |
| 6,051,259 A | | 4/2000 | Johnson et al. |

OTHER PUBLICATIONS

LiZL; Zhang NZ, Nie YH, Accelerated thrommbolysis by Liposomal–encapsulated urokinase in a canine model of acute myocardial infarcation National Library of Medicine: IGM Full Record Screen.

W.R. Perkins, D.E. Vaughan, S.R. Plavin, W.L. Daley, J. Rauch, L. Lee, A.S. Janoff, "Streptokinase Entrapment in Interdigitation–Fusion Liposomes Improves Thrombolysis in an Experimental Rabbit Model", Thromb Haemost, 1997, 77: 1174–8.

Phillip D. Nguyen, Edgar A. O'Rear, Arthur E. Johnson, Eugene Patterson, Thomas L. Whitsett and Remesh Bhakta, "Accelerated Thrombolysis and Reperfusion in a Canine Model of Myocardial Infarction by Liposomal Encapsulated of Streptokinase", Circulation Research, Mar. 1990, vol. 66, No. 3, p. 875–878.

J.L. Heeremans, R. Prevost, M.E. Bekkers, P. Los, J.J. Emeis, C. Kluff and D.J. Crommelin, "Thrombolytic Treatment with Tissue–type Plasminogen Activator (t–PA) containing Liposomes in Rabbits: a Comparison with Free t–PA", Thromb Haemost, Mar. 1995; 73(3); p. 488–494.

(List continued on next page.)

Primary Examiner—James M. Spear
Assistant Examiner—Liliana Di Nola-Baron
(74) Attorney, Agent, or Firm—Dunlap, Codding & Rogers, P.C.

(57) ABSTRACT

A drug delivery system which includes a plurality of microcapsules, each microcapsule containing a plasminogen activator entrapped in a biocompatible, biodegradable, substantially water-soluble polymeric matrix such that the plasminogen activator is releasable therefrom upon exposure of the microcapsules to an aqueous environment, as well as methods for preparing same. Methods of treating a thrombotic condition and reducing the time required for reperfusion of an occluded blood vessel are also described, which include parenterally administering to a mammal a therapeutically effective amount of a pharmaceutical composition which includes a plurality of such microcapsules.

21 Claims, 2 Drawing Sheets

Effect of Encapsulation on Initial Reperfusion Time

OTHER PUBLICATIONS

Smadar Cohen, Toshio Yoshioka, Melissa Lucarelli, Lena H. Hwang and Robert Langer, "Controlled Delivery Systems for Proteins Based on Poly (lactic/Glycolic Acid Microspheres", Pharmaceutical Research, 1991, vol. 8, No. 6, p. 713–720.

P.D. Nguyen, E.A. O'Rear, A.E. Johnson, R. Lu and B.M. Fung, "Thrombolysis Using Liposomal–Encapsulated Streptokinase: An In Vitro Study (42995)", P.S.E.B.M. 1989, vol. 192, p. 261–269.

Tiffany Medlin Osborn, M.D., Marian P. LaMonte, M.D., MSN, and Wade R. Gaasch, M.D., "Intravenous Thrombolytic Therapy for Stroke: A Review of Recent Studies and Controversies", Annals of Emergency Medicine, Aug. 1999 34:2, p. 244–255.

Thomas G. Kwiatkowski, M.D., Richard B. Libman, M.D., Michael Frankel, M.D., Barbara C. Tilley, Ph.D., Lewis B. Morgenstern, M.D., Mei Lu, Ph.D., Joseph P. Broderick, M.D., Christopher A. Lewandowski, M.D., John R. Marler, M.D., Steven R. Levine, M.D., and Thomas Brott, M.D., "Effects of Tissue Plasminogen Activator For Acute Ischemic Stroke At One Year", New England Journal of Medicine, Jun. 10, 1999, vol. 340, p. 1781–1787.

Jung–He Wu, Khalid Siddiqui and Scott L. Diamond, "Transport Phenomena and Clotdissolving Therapy: An Experimental Investigation of Diffusion–Controlled and Permeation–enhanced Fibrinolysis", Thromb Haemost, Jul. 1994; 72 (1), p. 105–112.

T.R. Tice and D.R. Cowsar, "Biodegradable controlled–release parenteral systems", Pharmaceutical Technology, Nov., 1964, vol. 8, Issue 11, p. 26–35.

Toyomi Sato, Motoko Kanke, Hans G. Schroeder and Patrick Deluca, "Porous Biodegradable Microspheres for Controlled Drug Delivery. I. Assessment of Processing Conditions and Solvent Removal Techniques", Pharmaceutical Research, vol. 5, No. 1980, pp. 21–30.

Lee R. Beck, Ph.D., Donald R. Cowsar, Ph.D., Danny H. Lewis, Ph.D., Robert J. Cosgrove, Jr., Ph.D., Charles T. Riddle, B.S., Suzanne L. Lowry, B.S. and Thomas Epperly, B.S., "A New Long–Acting Injectable Microcapsule System For the Administration of Progesterone", Fertility and Sterility, May 1979, vol. 31, No. 5, P. 545–551.

Jeffrey L. Cleland, "Solvent Evaporation Processes for the Production of Controlled Release Biodegradable Microsphere Formulations for therapeutics and Vaccines", Biotechnol Prog., 1998, vol. 14, p. 102–107.

Jeffrey L. Cleland, "Protein Delivery from Biodegradable Microspheres", in Protein Delivery: Physical Systems, Sanders and Hendren, eds., Plenum Press, New York, 1997, p. 1–43.

\* cited by examiner

MICROENCAPSULATED PLASMINOGEN ACTIVATORS

CROSS-REFERENCE TO RELATED APPLICATIONS

This application is a continuation of U.S. Ser. No. 09/592,482, entitled "MICROENCAPSULATED PLASMINOGEN ACTIVATORS", filed Jun. 9, 2000; now abandoned which claims the benefit under 35 U.S.C. 119(e) of provisional application U.S. Serial No. 60/139,322 entitled "MICROENCAPSULATED PLASMINOGEN ACTIVATOR" filed Jun. 10, 1999.

STATEMENT REGARDING FEDERALLY SPONSORED RESEARCH OR DEVELOPMENT

Not Applicable.

BACKGROUND OF THE INVENTION

Field of the Invention

The present invention relates generally to methods of treatment and pharmaceutical compositions, and more particularly, but not by way of limitation, to delivery systems for pharmaceutical compositions.

SUMMARY OF THE INVENTION

According to the present invention, pharmaceutical compositions comprising a plurality of microcapsules suitable for parenteral injection into a mammal, as well as methods for preparing same, are provided. Broadly, the microcapsules comprise a plasminogen activator entrapped in a biocompatible, biodegradable, substantially water-soluble polymeric matrix.

The present invention relates to a method of treating a thrombotic condition in a mammal in need of such therapy, and such method includes parenterally injecting into the mammal a therapeutically effective amount of a pharmaceutical composition, wherein the pharmaceutical composition is composed of a plurality of microcapsules, each microcapsule comprising a plasminogen activator entrapped in a biocompatible, biodegradable, substantially water-soluble polymeric matrix.

The present invention also relates to a method of reducing the time required for reperfusion of an artery containing a thrombus in a mammal as compared with the reperfusion time of an artery in a mammal administered an equal amount of a plasminogen activator in free form or an equal amount of a liposome-encapsulated plasminogen activator. Broadly, the method includes parenterally injecting into the mammal a therapeutically effective amount of a pharmaceutical composition, wherein the pharmaceutical composition is composed of a plurality of microcapsules, each microcapsule comprising a plasminogen activator entrapped in a biocompatible, biodegradable, substantially water-soluble polymeric matrix.

An object of the present invention is to provide a pharmaceutical composition which provides rapid delivery of a plasminogen activator to an occluded blood vessel.

Another object of the present invention, while achieving the before-stated object, is to provide a process for preparing such pharmaceutical composition.

Another object of the present invention, while achieving the before-stated objects, is to provide a method for treatment of a thrombotic condition in a mammal comprising injecting into the mammal a therapeutically effective amount of such pharmaceutical composition.

Other objects, features and advantages of the present invention will become apparent from the following detailed description when read in conjunction with the accompanying drawings and appended claims.

DETAILED DESCRIPTION OF THE INVENTION

Figure 1:
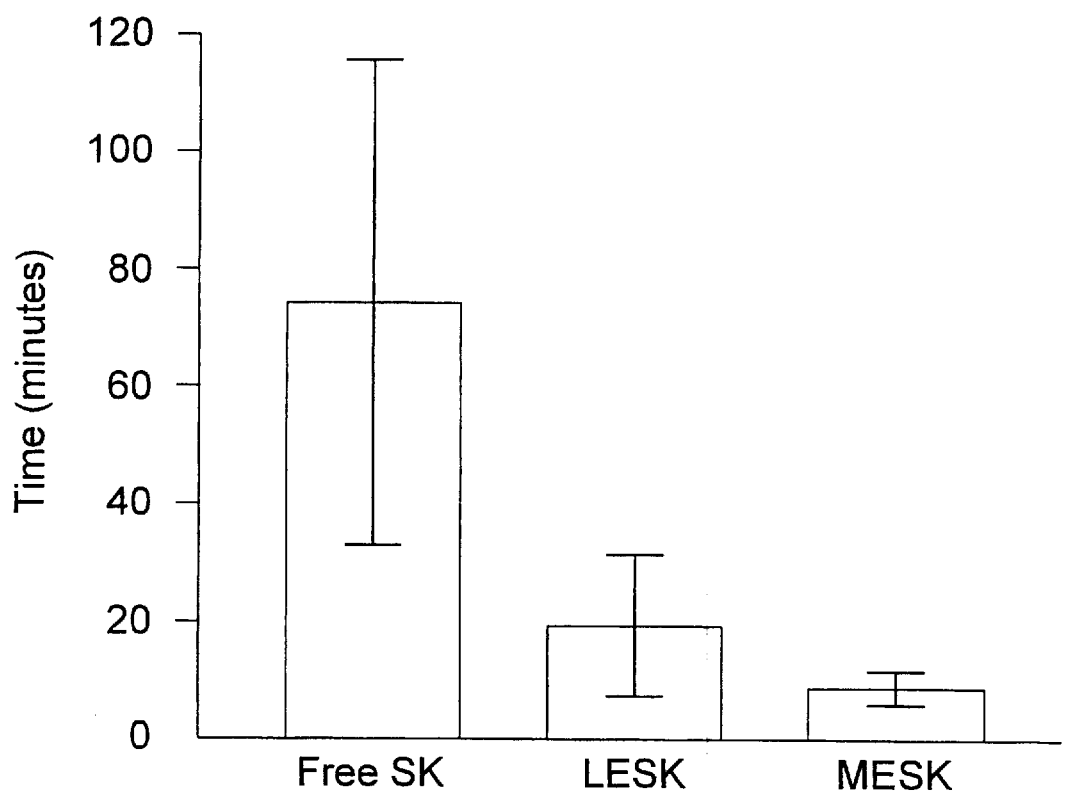
FIG. 1 is a graphic depiction demonstrating the initial reperfusion time of unencapsulated streptokinase (Free SK), liposome-encapsulated streptokinase (LESK) and streptokinase microencapsulated in a polyethylene glycol matrix (MESK).

The formation of an occlusive thrombus in a vessel can damage tissue normally supplied nutrients by the flow of blood through that vessel. If the occlusive thrombus is formed within a coronary artery, an acute myocardial infarction may be precipitated, whereas if the occlusive thrombus is lodged in an artery which supplies blood to the brain, an ischemic stroke may occur, and either condition can be fatal to the patient. Time is of critical importance in treating such conditions, and in general, thrombolytic therapy is believed to be beneficial to recovery for a period up to six hours in myocardial infarction patients and three hours in stroke patients following initiation of symptoms.

Conventional thrombolytic therapy with plasminogen activators such as streptokinase, urokinase and tPA (tissue plasminogen activator), requires thirty minutes to one hour or longer to reestablish blood flow, which can result in considerable tissue loss during and following the treatment period. Therefore, an acceleration in the thrombolytic activity of a plasminogen activator would be beneficial in treating myocardial infarction and ischemic stroke patients.

In addition, the potential of serious side effects, such as life-threatening uncontrolled bleeding, accompanies the use of plasminogen activators, as large concentrations of such drugs must be given. As many of the drugs are derived from bacterial cell cultures, an immune response can be generated in a patient that has previously been exposed to the bacteria, and therefore higher concentrations of the drug must be given in order to overwhelm the resulting antibodies. Further, as proteins, plasminogen activators are extremely sensitive to enzymatic digestion as well as changes in the surrounding environment, such as changes in temperature and acidity, and thus have short half-lives. The high dosages of plasminogen activators required to overcome these problems can lead to undesired hemorrhages throughout the body. Therefore, reduction of the dosage of the plasminogen activator can reduce the potential for these adverse side effects.

Encapsulation of thrombolytic agents was proposed as a method to circumvent several of these problems. Firstly, encapsulation would act as a shield for the protein to avoid deactivation by the body and would therefore extend the half-life of the drug. This would allow the drug to circulate in the body longer and reach its destination in order to dissolve the blood clot. The increased circulation time permits the administration of a lower total dosage of the drug, thereby resulting in a lessened possibility for harmful side effects.

One method of increasing the thrombolytic activity of a plasminogen activator while reducing the amount of plasminogen activator required is described in U.S. Pat. No. 5,503,850 entitled "METHOD AND COMPOSITION FOR THE TREATMENT OF THROMBOSIS IN A MAMMAL" issued to O'Rear et al on Apr. 2, 1996, the Specification of which is hereby expressly incorporated by reference herein. Such method involves encapsulating a plasminogen activator in a liposome. Encapsulation of streptokinase in liposomes decreased the time necessary to restore blood flow in a canine coronary artery model by 41% over the free infusion of the drug (78±43 minutes to 32±28 minutes).

However, commercial use of liposomes in drug delivery has not been extensively employed for several reasons. The primary reason is due to the lack of stability of the vesicles, as liposomes tend to maintain their integrity in an aqueous environment for only about 48 hours. After this time, the oxidation of the fatty acid molecules that compose the backbone of the liposome compromises the wall of the liposome, and the drug material is allowed to leak from the liposome. Since the time required to prepare liposome-encapsulated drugs can be up to five days in some instances, the two days of stability obtained is typically prohibitive of their use. In order to be truly effective, the liposome-encapsulated drugs would need to be prepared on sight and used within the 48-hour period or disposed. Although this technique may be feasible for research purposes, the majority of clinicians do not find this to be a practical solution to improved delivery of plasminogen activators, and thus liposome-encapsulated plasminogen activators have not been extensively employed in the commercial environment.

Other drug delivery systems which include microencapsulated pharmaceuticals are known in the art and involve the use of polymer encapsulated drug delivery systems. However, such drug delivery systems were designed to provide controlled release of a drug contained therein over a period of time such as weeks or even months and therefore prevent the need for repeated, often daily, injections of such drugs. Such controlled release drug delivery systems utilize substantially water-insoluble polymers for forming such vehicles to extend the release rate of the drug from the vehicle, and therefore do not produce a vehicle which will dissolve quickly and deliver the drug to the site of injury at a rate faster than the rate observed for free infusion of the drug alone. Such drug delivery systems typically employ polymers such as poly(lactide-co-glycolide) (PLGA), poly (lactic acid) (PLA) or poly(glycolic acid) (PGA) which are not soluble in aqueous solutions, and therefore the pharmaceuticals contained therein are only released by simple diffusion through the matrix or following degradation of the polymer, thus resulting in controlled release of the drug contained therein over a period of time such as weeks or even months, rather than rapid and accelerated delivery of the drug. In fact, such compositions are formulated to reduce the initial release phase of the drug.

An example of such a drug delivery system which utilizes a substantially water-insoluble polymer for encapsulating a drug therein is described in U.S. Pat. No. 6,051,259 entitled "COMPOSITION FOR SUSTAINED RELEASE OF HUMAN GROWTH HORMONE" issued to Johnson et al on Apr. 18, 2000, the Specification of which is hereby expressly incorporated herein by reference, which describes a composition for the sustained release of human growth hormone from a polymer matrix comprising PLGA.

The present invention is directed to a composition which includes a plurality of microcapsules suitable for parenteral injection into a mammal such as a human wherein the microcapsules each comprise a plasminogen activator entrapped in a biocompatible, biodegradable, substantially water-soluble polymeric matrix. Such microcapsules provide the benefits seen with the prior art drug delivery systems which employ liposome-encapsulated plasminogen activators but overcome the disadvantages of such prior art drug delivery systems.

The present invention also relates to a method of treating a thrombotic condition in a mammal in need of such therapy, wherein the method includes parenterally injecting into the mammal a therapeutically effective amount of a pharmaceutical composition. The pharmaceutical composition employed in such method comprising a plurality of microcapsules, wherein each microcapsule has a plasminogen activator entrapped in a biocompatible, biodegradable, substantially water-soluble polymeric matrix. Administration of the microcapsules of the present invention reduces by at least about 60% the time required to reperfuse the blood vessel as compared to the time required using an equivalent amount of the plasminogen activator in free form.

The present invention is also directed to a method of reducing the time required for reperfusion of an artery containing a thrombus in a mammal as compared with the reperfusion time of an artery observed when a mammal is administered an equal amount of a plasminogen activator in free form or an equal amount of a liposome-encapsulated plasminogen activator. Such a method resulting in a reduced reperfusion time includes parenterally injecting into the mammal a therapeutically effective amount of a pharmaceutical composition, wherein the pharmaceutical composition comprises a plurality of microcapsules, each having a plasminogen activator entrapped in a biocompatible, biodegradable, substantially water-soluble polymeric matrix. Administration of the microcapsules of the present invention reduces by at least about 60% the time required to reperfuse the blood vessel as compared to the time required using an equivalent amount of the plasminogen activator in free form.

The term "plasminogen activator" as used herein will be understood to include streptokinase, urokinase and tPA, any recombinant form thereof, and any combination thereof, as well as variants thereof, such as derivatives, conjugates, analogs and fragments thereof which retain at least a portion of the thrombolytic activity of streptokinase, urokinase or tPA, including acylated plasminogen streptokinase activator complex and Ancrod. The term "plasminogen activator" as used herein will also be understood to include any peptide or polypeptide fragments of streptokinase, urokinase or tPA which possess thrombolytic activity as well as variants of such peptide or polypeptide fragments which contain one or more conserved or unconserved amino acid substitutions or one or more amino acid insertions or deletions therein and which retain at least a portion of such thrombolytic activity. The manipulations which result in the production of the derivatives, conjugates, analogs, fragments and variants of the proteins, peptides or polypeptides can occur at the transcriptional, post-transcriptional or post-translational levels.

The term "plasminogen activator" may be used interchangeably herein with the terms "thrombolytics", "thrombolytic agents" and "clot-busting drugs".

As previously stated, the composition of the present invention includes a plurality of microcapsules, each having a plasminogen activator encapsulated in a biocompatible, biodegradable, substantially water-soluble polymeric matrix. The term "biodegradable, substantially water-soluble polymer matrix" as used herein refers to a matrix formed of a biocompatible, biodegradable, substantially water soluble polymer which typically has a low molecular weight. The term "substantially water soluble polymer" as used herein refers to a polymer which dissolves in an aqueous environment, such as physiological conditions, in a shorter period of time than is required to dissolve a blood clot under normal free plasminogen activator infusion conditions. The time required for dissolution of the polymer may be in the range of about instantaneously to about two hours, and preferably less than about 30 minutes.

The term "biocompatible polymer" as used herein will be understood to refer to a polymer which is non-toxic to the recipient and also presents no deleterious or untoward effects on the recipient's body, such as an immunological reaction at the injection site. The term "biocompatible polymer" as used herein also means that any degradation products of the polymer must also be non-toxic and present no deleterious or untoward effects.

The term "biodegradable polymer" as used herein refers to a polymer which will degrade or erode in vivo to form smaller chemical species. Degradation can result, for example, by enzymatic, chemical and physical processes.

In addition, the biocompatible, biodegradable, substantially water-soluble polymer must not denature the protein encapsulated therein, nor interact with the protein, thereby altering the rate of protein release from the microcapsule, nor alter the pharmacological properties of the drug. The biocompatible, biodegradable, substantially water-soluble polymer must be capable of being produced with consistent properties that are readily quantifiable and reproducible. Further, the microcapsule formed of the biocompatible, biodegradable, substantially water-soluble polymer must form a powder upon exposure to the preparation process described in detail herein below.

Examples of such biocompatible, biodegradable, substantially water-soluble polymers include polyethylene glycol, polyethylene oxide, dextran, and combinations thereof, as well as comparable polymers which have a similar molecular weight in the range of from about 10,000 to about 30,000. The use of a combination of two or more polymers may result in a matrix which has different properties than a matrix formed of either of the two polymers alone. Preferably, the biocompatible, biodegradable, substantially water-soluble polymer is polyethylene glycol (PEG) having a molecular weight in the range of from about 10,000 to about 30,000, which is inexpensive, nontoxic, biodegradable, nonimmunogenic, and has already been approved for intravenous use by the Food and Drug Administration (FDA). In addition, polyethylene glycol begins to dissolve immediately upon exposure to an aqueous environment, and dissolution thereof is in a range of from about five to about thirty minutes under physiological conditions.

The microcapsules of the present invention must exist in the form of a fine powder and are prepared by mixing the plasminogen activator and the biocompatible, biodegradable, substantially water-soluble polymer as described in more detail herein below. The plasminogen activator is entrapped in the biocompatible, biodegradable, substantially water-soluble polymeric matrix such that a matrix-type microparticle is formed in which the plasminogen activator is dispersed throughout the polymeric matrix. Since the polymeric matrix is substantially water-soluble, the plasminogen activator is released into the cardiovascular system upon dissolution of the polymeric matrix, as opposed to the prior art microcapsule delivery systems which utilize substantially water-insoluble polymers and therefore require the drug entrapped therein to diffuse through the microcapsule or wait until at least a portion of the polymer degrades to be released therefrom.

The method of forming the microcapsules of the present invention involves mixing the biocompatible, biodegradable, substantially water-soluble polymer dissolved in a solvent with an aqueous solution containing a plasminogen activator to provide an emulsion, adding an emulsifying solution to stabilize the emulsion, and evaporating the aqueous solution prior to dissolution of the biocompatible, biodegradable, substantially water-soluble polymer in the aqueous solution, thereby forming a microcapsule in which the plasminogen activator is encapsulated in a biocompatible, biodegradable, substantially water-soluble polymeric matrix.

A suitable polymer solution, containing the biocompatible, biodegradable, substantially water-soluble polymer dissolved in a suitable polymer solvent, preferably contains between about 1% (w/w) and about 80% (w/w) of the biocompatible, biodegradable, substantially water-soluble polymer. A suitable polymer solvent, as defined herein, is a solvent in which the polymer is soluble but in which the plasminogen activator is substantially insoluble and non-reactive. Examples of suitable polymer solvents include polar organic liquids such as methylene chloride, chloroform, ethyl acetate and acetone. Preferably, a specific mass of polymer, such as 10,000 MW polyethylene glycol, is dissolved in a volume of chloroform, wherein the volume of chloroform is in a range of from about 1.0 ml to about 1.5 ml.

An aqueous solution containing a plasminogen activator is formed by dissolving an effective amount of plasminogen activator in distilled water. Preferably, about 10,000 IU to about 50,000 IU of streptokinase is dissolved in 250 microliters of distilled water.

The suitable polymer solution and the aqueous solution containing the plasminogen activator are mixed or agitated to form an emulsion. One method of mixing the two solutions is by sonication. Sonication methods are well known in the art, and therefore no further explanation of such methods are required. Preferably, the mixture containing the suitable polymer solution and the aqueous solution containing the plasminogen activator are sonicated at 40–50 watts for about 30 seconds to about 1 minute.

Following mixing of the two solutions to form an emulsion, an emulsifying solution may be added to stabilize the emulsion, and this combination is vortexed. Examples of emulsifying solutions include poly(vinyl alcohol), Tween-80, polysorbate 80 (glycol), and other like compounds. Preferably, poly(vinyl alcohol) (PVA) is added to the sonicated mixture, and this combination is vortexed for at least about 10 seconds.

Once the emulsion is formed, a cross-linking agent may be added to extend the dissolution time of the polymer. Examples of cross-linking agents include glutaraldehyde and other like aldehyde compounds. Optionally, a cross-linking agent may be omitted from the protocol.

Following mixing of the suitable polymer solution and the aqueous solution containing the plasminogen activator and addition of the emulsifying solution and the cross-linking agent, the resulting mixture is placed in a low temperature freezer. The period of time for exposure to this temperature may vary, but is desirably at least about 30 minutes. The low temperature freezer maintains a temperature which is lower than about −70° C. and is preferably about −80° C.

The frozen mixture is then allowed to freeze dry for at least about 12 hours. The temperature at which freeze-drying occurs is in a range of from about −30° C. to about −60° C. The method of freeze-drying is well known in the art, and therefore no further explanation of such method need be described. The frozen mixture results in the formation of microcapsules, which are in the form of an aggregate. A gentle break-up procedure may be employed to separate the microcapsules. Such procedures are known in the art, and therefore no further description of such procedures need be required.

The term "freeze-drying" may be used interchangeably herein with the term "lyophilization".

Following lyophilization, the microcapsules are washed in a nonsolvent such as hexane and filtered under a vacuum. The resulting powder containing microcapsules is then evaluated for encapsulation efficiency. In the Example described herein below, encapsulation efficiency was determined using a Chrom-Z-PLG® kit obtained from Helena Laboratories, Beaumont, Tex.

It will be understood that while a preferred embodiment of preparing the microcapsules of the present invention has been presented herein, numerous changes to the method may be made which will readily suggest themselves to one skilled in the art, and therefore the microcapsules may be prepared by another method which is within the scope of the invention if such method involves the rapid removal of water from the emulsion to prevent dissolution of the biocompatible, biodegradable, substantially water-soluble polymer in the aqueous solution.

The microcapsules of the present invention must be small enough to not lodge in a blood vessel and cause a blockage of flow. The microcapsules must also be nontoxic, biodegradable, nonimmunogenic and stable in a refrigerated environment for a considerably longer period of time than the liposome-encapsulated plasminogen activators of the prior art. The microcapsules of the present invention may be of any size suitable for intravenous injection and capable of having a plasminogen activator-containing polymeric matrix. Preferably, the microcapsules have a particle size in a range of from about 250 angstroms to about 20 micrometers. More preferably, the microcapsules have a particle size in a range of from about 5 to about 10 micrometers.

The ratio of biocompatible, biodegradable, substantially water-soluble polymer to plasminogen activator in the microcapsules of the present invention may vary as long as the microcapsules exist in the form of a powder suitable for parenteral injection into a mammal, dissolve rapidly and result in release of the plasminogen activator within the cardiovascular system of the mammal such that the plasminogen activator is delivered to the site of injury in a period of time which is less than the time required using an equivalent amount of the plasminogen activator in free form. However, desirably the polymer:drug ratio may be in a range of from about 200:1 to about 5:1.

The microcapsules of the present invention have been evaluated for thrombolytic activity using an in vivo model of carotid stroke in rabbits, which is described in detail in The Example. The model involves anesthetizing New Zealand white rabbits of either sex with inhaled isoflorane (about 5%) and maintaining the rabbit with about 3% to about 5% isoflorane. Cardiac activity is monitored by electrocardiogram. The right carotid artery is isolated, as is the left jugular vein. The jugular vein is cannulated with PE-90 tubing, which is connected to a 20-cc syringe. Right carotid artery flow is measured with a 20-MHz pulsed Doppler or electromagnetic flow probe. Arterial thrombosis is initiated by the injection of about 100 units thrombin and about 0.1-ml whole blood into a 5–10-mm long segment of proximal and distal right carotid artery. After about 10 ensnared minutes, the proximal ligature is released; after an additional about 5 minutes, the distal ligature also is released. The thrombus is allowed to mature for about 30 minutes prior to administration of streptokinase. Animals are observed for about 2 hours following the initiation of infusion.

The acceleration of thrombolytic activity can be shown by several factors, such as a decrease in the amount of time required to dissolve a thrombus or by a decrease in the amount of time required for reperfusion. In the Example, reperfusion time in the rabbit model was determined by a resolution of electrocardiographic changes induced by ischemia and recovery of right carotid arterial flow. In addition, at the conclusion of the experiment, the right carotid artery is dissected, and the thrombus mass is determined gravimetrically.

The acceleration of thrombolysis decreased the amount of time required to reperfuse an artery occluded with a thrombus. The rate of acceleration of thrombolysis of the PEG-encapsulated plasminogen activator of the present invention is at least about 60% faster than the rate of thrombolysis in a mammal administered a composition comprising unencapsulated plasminogen activator, and at least about 50% faster than the rate of thrombolysis in a mammal administered a composition comprising liposome-encapsulated plasminogen activator. In the Example described herein below and in the data derived therefrom which is depicted in FIG. 1, the rate of acceleration of thrombolysis of the PEG-encapsulated plasminogen activator of the present invention is at least about 88% faster than the rate of thrombolysis in a mammal administered unencapsulated plasminogen activator (9±3 minutes to 74±41 minutes), and at least about 53% faster than the rate of thrombolysis in a mammal administered a composition comprising liposome-encapsulated plasminogen activator (9±3 minutes to 19±12 minutes).

The microcapsules of the present invention may be dissolved in a fluid medium suitable for parenteral injection, such as intravenous injection into a mammal, in which the microcapsules are suspended. The carrier should be sterile, have an osmolality and a pH range suitable for injection in a subject, and be relatively inert, i.e., permit the composition to retain at least a portion of the thrombolytic activity. Some examples of suitable carriers are sterile normal saline, 5% sterile dextrose in water, and combinations thereof.

The dose of the encapsulated plasminogen activator of the present invention can follow standard dosage requirements, i.e., dosages set by plasminogen activator manufacturers or researchers. For example, in myocardial infarction, a dose of 1.5 million units of streptokinase in solution is infused over one hour or 30 units of acylated-plasminogen-streptokinase-activator-complex (APSAC) over 3–5 minutes. In stroke, for example, a dose of about 0.9 mg/kg (with a maximum dose of about 90 mg) in solution is given as a bolus of about 10% followed by delivery of the remaining about 90% as a constant infusion over a period of about 60 minutes.

Figure 2:
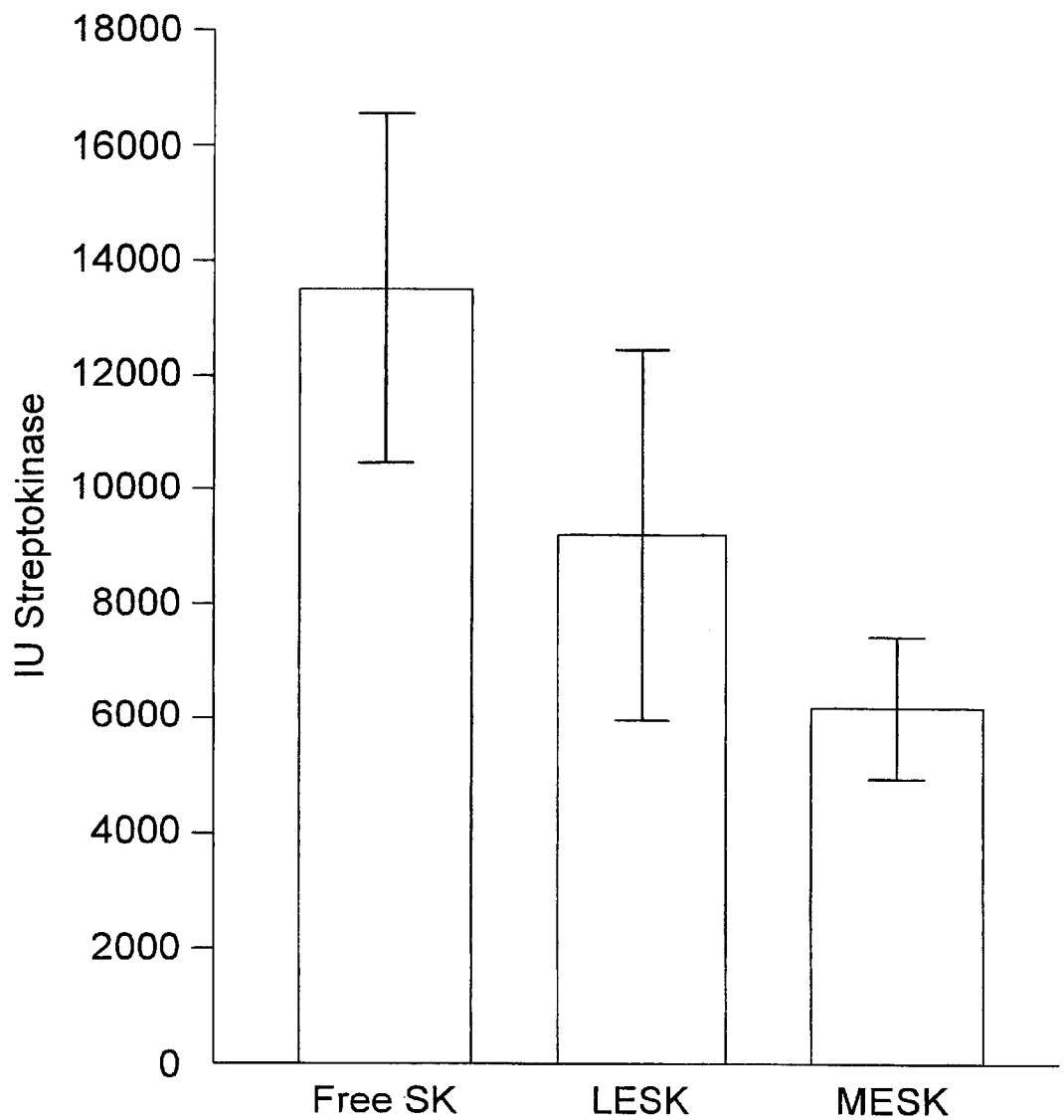
FIG. 2 is a graphic depiction demonstrating the total amount of units of streptokinase delivered as Free SK, LESK and MESK required to reperfuse the induced thrombus in an in vivo rabbit model of carotid stroke.

However, one of the advantages of the microcapsules of the present invention is that encapsulation of plasminogen activators reduces the minimum therapeutically effective amount of plasminogen activator required to reperfuse an artery occluded by a thrombus by at least about 10% as compared with the minimum effective dosage of free plasminogen activator, i.e., plasminogen activator which is not encapsulated. As previously stated, the reduction in the dose of the plasminogen activator can reduce the risk of adverse side effects. Additionally, the cost of the plasminogen activator to the patient is reduced. As shown in FIG. 2, encapsulation of the plasminogen activator in the microcapsules in accordance with the present invention reduced the minimum therapeutically effective amount of plasminogen activator required to reperfuse an artery occluded by a thrombus from about 13,500 IU/kg for free streptokinase to about 6,200 IU/kg for the microencapsulated streptokinase, resulting in a reduction of about 54%.

The following Example is set forth to illustrate the preparation and use of the encapsulated plasminogen activator of the present invention. However, it is to be understood that the Example, the composition prepared therein as well as the use of such composition is for illustrative purposes only and is not to be considered as limiting the scope of the present invention.

EXAMPLE

An in vivo study was performed wherein arterial thrombi were prepared and then used to analyze the action in a reperfusion study of free streptokinase (SK), liposome-encapsulated streptokinase (LESK), and streptokinase microencapsulated in a polyethylene glycol matrix (MESK).

Methods and Materials

About 1 g of 10,000 MW polyethylene glycol was dissolved in about 1.25 ml to about 1.5 ml of chloroform. About 40,000 IU streptokinase was dissolved in about 250 microliters of distilled water. The two solutions were combined and sonicated at about 40 to about 50 watts for about 45 seconds to about 1 minute. The protein/polymer mixture was added to about 1 ml of 2% PVA, an emulsifying solution, and the resulting mixture was then vortexed for about 20 seconds. About 250 microliters of glutaraldehyde, a cross-linking agent, was added, and the mixture was vortexed for about 10 seconds. The final mixture was placed in a freezer maintained at a temperature of about −80° C. for at least about 30 minutes to produce a frozen mixture. The frozen mixture was then allowed to freeze-dry at about −30° C. to about −60° C. for at least about 12 hours. Following lyophilization, the dried mixture was washed in a centrifuge twice in hexane (3,000 rpm for about 2 minutes each) and filtered under a vacuum.

Following the preparation of the formulation and determination of encapsulation efficiency using a Chrom-Z-PLG® kit obtained from Helena Laboratories, Beaumont, Tex., the microencapsulated streptokinase was tested in an in vivo model of carotid stroke. New Zealand white rabbits of either sex were anesthetized with inhaled isoflurane (5%) and maintained on 3–5% isoflurane. Cardiac activity was monitored by ECG. The right carotid artery was isolated, as was the left jugular vein. The jugular vein was cannulated with PE-90 tubing, which was connected to a 20-cc syringe. Right carotid artery flow was measured with a 20-MHz pulsed Doppler or electromagnetic flow probe. Arterial thrombosis was initiated by the injection of 100 units thrombin and 0.1-ml whole blood into a 5–10-mm long segment of proximal and distal right carotid artery. After 10 ensnared minutes, the proximal ligature was release; after an additional 5 minutes, the distal ligature also was released. In some experiments, as many as three injections were necessary to form an occlusive thrombus. The thrombus was allowed to mature for 30 minutes prior to administration of SK.

The relative dosages of the two thrombolytic preparations were identical. A dosage of 6, units/kg was determined as adequate to produce thrombolysis. The preparation was dispersed in normal saline to a total volume of 20 cc. An initial bolus of 20% (4 ml) preceded a constant intravenous infusion of the remaining 80% over a 30 minute time period. The infusion was maintained at a steady rate with an infusion pump. Animals were observed for 2 hours following the initiation of infusion. Reperfusion was documented by 1) a resolution of electrocardiographic changes induced by ischemia, and 2) recovery of right carotid arterial flow. At the conclusion of the experiment, the artery was dissected, and thrombus mass was determined gravimetrically.

Results

Rabbits were monitored for the time required to restore initial blood flow, defined as 10% of the original carotid arterial flow, as well as for any physiological difficulties with the formulation. For the infusion of 6000 IU/kg of free streptokinase, the time required to obtain initial reperfusion was found to be 74±41 minutes (mean±S.D.). Upon encapsulation of a similar dosage of the plasminogen activator in the liposome, the time was reduced to 19±12 minutes. Upon encapsulation of a similar dosage of the plasminogen activator into the polymer formulation, the time was reduced to 9±3 minutes.

The determination of flow restoration was made by observing the results obtained by a Doppler flow probe. The readings from the flow probe were illustrated on graph paper. The blood flow was monitored to determine the time to restore at least 10% of the original flow, based on the initial carotid blood flow (prior to clot insertion). Cardiac activity was simultaneously represented on the graph paper.

None of the animals exhibited physiological difficulties with uncontrolled hemorrhaging from the injury site. In five of six experiments, the animal regained 100% of the original blood flow through the previously occluded blood vessel. In the sixth experiment, the rabbit exhibited a return of 50% of the original blood flow.

While the use of a biocompatible, biodegradable, substantially water-soluble polymeric matrix as a delivery system for plasminogen activators has been disclosed herein, it will be understood that the biocompatible, biodegradable, substantially water-soluble polymeric matrix could be applied in efforts to encapsulate any drug that should be delivered rapidly and which degrades in the body. Therefore, the use of the biocompatible, biodegradable, substantially water-soluble polymeric matrix to encapsulate other drugs for such uses is provided in the scope of the present invention, and as such the present invention is not limited to drug delivery systems for plasminogen activators.

From the above description, it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A composition for rapid and accelerated delivery of a pharmaceutical compound comprising a plurality of microcapsules, wherein each of the microcapsules contain a therapeutically effective amount of the pharmaceutical compound entrapped in a biocompatible, biodegradable, substantially water-soluble polymeric matrix formed of a biocompatible, biodegradable, substantially water-soluble polymer having a molecular weight in a range of from about 10,000 to about 30,000, and wherein the biocompatible, biodegradable, substantially water-soluble polymeric matrix and the microcapsules formed therefrom begin to dissolve immediately upon exposure to an aqueous environment such that complete dissolution thereof occurs in less than about two hours under physiological conditions.

2. The composition of claim 1 wherein the biocompatible, biodegradable, substantially water-soluble polymeric matrix is formed of a polymer selected from the group consisting of polyethylene glycol, polyethylene oxide, dextran, and combinations thereof.

3. The composition of claim 1 wherein the pharmaceutical compound is a plasminogen activator.

4. A method for rapid and accelerated delivery of a pharmaceutical compound comprising parenterally administering to a mammal a therapeutically effective amount of a pharmaceutical compound disposed in a plurality of microcapsules, wherein each of the microcapsules comprises the pharmaceutical compound entrapped in a biocompatible, biodegradable, substantially water-soluble polymeric matrix formed of a biocompatible, biodegradable, substantially water-soluble polymer having a molecular weight in a range of from about 10,000 to about 30,000, and wherein the biocompatible, biodegradable, substantially water-soluble polymeric matrix and the microcapsules formed therefrom begin to dissolve immediately upon exposure to an aqueous environment such that complete dissolution thereof occurs in less than about two hours under physiological conditions.

5. The method of claim 4 wherein the biocompatible, biodegradable, substantially water-soluble polymeric matrix is formed of a polymer selected from the group consisting of polyethylene glycol, polyethylene oxide, dextran, and combinations thereof.

6. The method of claim 4 wherein the pharmaceutical compound is a plasminogen activator.

7. A delivery system comprising a plurality of microcapsules, wherein each of the microcapsules comprises:
    a plasminogen activator;
    a biocompatible, biodegradable, substantially water-soluble polymeric matrix formed of a biocompatible, biodegradable, substantially water-soluble polymer having a molecular weight of from about 10,000 to about 30,000; and
    wherein the plasminogen activator is entrapped in the biocompatible, biodegradable, substantially water-soluble polymeric matrix to form the microcapsules, and wherein the plasminogen activator is releasable from the biocompatible, biodegradable, substantially water-soluble polymeric matrix upon exposure of the microcapsules to an aqueous environment as dissolution of the biocompatible, biodegradable, substantially water-soluble polymeric matrix and the microcapsules formed therefrom occurs in less than about two hours under physiological conditions.

8. The delivery system of claim 7 wherein the time required for release of the plasminogen activator from the biocompatible, biodegradable, substantially water-soluble polymeric matrix upon exposure of the microcapsule to an aqueous environment is less than about 30 minutes.

9. The delivery system of claim 7 wherein the plasminogen activator is selected from the group consisting of streptokinase, urokinase, tPA, combinations thereof, derivatives thereof, conjugates thereof, fragments thereof and variants thereof.

10. The delivery system of claim 7 wherein the biocompatible, biodegradable, substantially water-soluble polymeric matrix is formed of a polymer selected from the group consisting of polyethylene glycol, polyethylene oxide, dextran, and combinations thereof.

11. The delivery system of claim 7 wherein the microcapsules have a size in a range of from about 250 angstroms to about 10 micrometers.

12. A method of preparing a delivery system comprising a plurality of microcapsules, wherein the method comprises:
    providing a biocompatible, biodegradable, substantially water-soluble polymer having a molecular weight of from about 10,000 to about 30,000 dissolved in a solvent;
    providing an aqueous solution containing a plasminogen activator;
    mixing the biocompatible, biodegradable, substantially water-soluble polymer dissolved in a solvent with the aqueous solution containing a plasminogen activator to produce an emulsion; and
    mixing an emulsifying solution with the emulsion to stabilize the emulsion;
    mixing a cross-linking agent with the emulsion to extend the dissolution time of the biocompatible, biodegradable, substantially water-soluble polymer; and
    evaporating the aqueous solution prior to dissolution of the biocompatible, biodegradable, substantially water-soluble polymer in the aqueous solution, thereby forming the microcapsules in which the plasminogen activator is encapsulated in a biocompatible, biodegradable, substantially water-soluble polymeric matrix.

13. The method of claim 12 wherein, in the step of providing the aqueous solution containing a plasminogen activator, the plasminogen activator is selected from the group consisting of streptokinase, urokinase, tPA, combinations thereof, derivatives thereof, conjugates thereof, fragments thereof and variants thereof.

14. The method of claim 12 wherein, in the step of providing the biocompatible, biodegradable, substantially water-soluble polymer dissolved in a solvent, the biodegradable, substantially water-soluble polymer is selected from the group consisting of polyethylene glycol, polyethylene oxide, dextran, and combinations thereof.

15. The method of claim 12 wherein, in the step of evaporating the aqueous solution, the aqueous solution is evaporated by freeze-drying.

16. A method of treating a thrombotic condition comprising parenterally administering to a mammal that has a thrombus within a blood vessel a therapeutically effective amount of a pharmaceutical composition comprising a plurality of microcapsules, each of the microcapsules comprising a plasminogen activator entrapped in a biocompatible, biodegradable, substantially water-soluble polymeric matrix formed of a biocompatible, biodegradable, substantially water-soluble polymer having a molecular weight in a range of from about 10,000 to about 30,000, and wherein the biocompatible, biodegradable, substantially water-soluble polymeric matrix and the microcapsules formed therefrom begin to dissolve immediately upon exposure to an aqueous environment such that complete dissolution thereof occurs in less than about two hours under physiological conditions, wherein the microcapsules are suitable for parenteral administration to the mammal to deliver the plasminogen activator to the thrombus.

17. The method of claim 16 wherein the plasminogen activator is selected from the group consisting of streptokinase, urokinase, tPA, combinations thereof, derivatives thereof, conjugates thereof, fragments thereof and variants thereof.

18. The method of claim 16 wherein the biocompatible, biodegradable, substantially water-soluble polymeric matrix is formed of a polymer selected from the group consisting of polyethylene glycol, polyethylene oxide, dextran, and combinations thereof.

19. A method of reducing the time required for reperfusion of a blood vessel containing a thrombus in a mammal as compared with the time required for reperfusion of a blood vessel containing a thrombus in a mammal when the mammal is administered an equal amount of a plasminogen activator in free form or an equal amount of a liposome-encapsulated plasminogen activator, the method comprising:

parenterally administering to the mammal a therapeutically effective amount of a pharmaceutical composition comprising a plurality of microcapsules, each of the microcapsules comprising a plasminogen activator entrapped in a biocompatible, biodegradable, substantially water-soluble polymeric matrix formed of a biocompatible, biodegradable, substantially water-soluble polymer having a molecular weight in a range of from about 10,000 to about 30,000, and wherein the biocompatible, biodegradable, substantially water-soluble polymeric matrix and the microcapsules formed therefrom begin to dissolve immediately upon exposure to an aqueous environment such that complete dissolution thereof occurs in less than about two hours under physiological conditions, wherein the microcapsules are suitable for parenteral administration to the mammal to deliver the plasminogen activator to the thrombus, wherein the plasminogen activator is delivered to the thrombus thereby reducing by at least about 60% the time required to reperfuse the blood vessel as compared to the time required using an equivalent amount of the plasminogen activator in free form.

20. The method of claim 19 wherein the plasminogen activator is selected from the group consisting of streptokinase, urokinase, tPA, combinations thereof, derivatives thereof, conjugates thereof, fragments thereof and variants thereof.

21. The method of claim 19 wherein the biocompatible, biodegradable, substantially water-soluble polymeric matrix is formed of a polymer selected from the group consisting of polyethylene glycol, polyethylene oxide, and combinations thereof.

* * * * *

UNITED STATES PATENT AND TRADEMARK OFFICE
CERTIFICATE OF CORRECTION

PATENT NO.    : 6,586,011 B2                                     Page 1 of 1
DATED         : July 1, 2003
INVENTOR(S)   : Jonathan K. Leach and Edgar O'Rear It is certified that error appears in the above-identified patent and that said Letters Patent is hereby corrected as shown below:

Title page,
Item [56], OTHER PUBLICATIONS, "LizL" reference, place quotation mark before the word "Accellerated"; also delete the word "thrommbolysis" and replace with the word -- thrombolysis --; and place quotation mark after the word "infarcation".

Column 9,
Line 60, change the word "release" to the word -- released --.
Line 67, change the number "6" to -- 6000 --.

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,586,011 B2
DATED : July 1, 2003
INVENTOR(S) : Jonathan K. Leach and Edgar O'Rear It is certified that error appears in the above-identified patent and that said Letters Patent is hereby corrected as shown below:

Title page,
Item [73], Assignee, delete "Southpac Trust International, Inc., Rarotonga (CK)" and replace with -- The Board of Regents of the University of Oklahoma, Norman, OK --.

Signed and Sealed this

Sixth Day of December, 2005

JON W. DUDAS
*Director of the United States Patent and Trademark Office*